United States Patent [19]
Vreeland

[11] 3,962,697
[45] June 8, 1976

[54] LOW LEVEL BIO-TELEMETRY SYSTEM USING C/MOS MULTIPLEXING

[75] Inventor: Robert Vreeland, San Francisco, Calif.

[73] Assignee: The United States of America as represented by the Secretary of the Navy, Washington, D.C.

[22] Filed: June 16, 1975

[21] Appl. No.: 587,172

[52] U.S. Cl. .............................. 340/183; 340/206; 307/251
[51] Int. Cl.² .......................................... G08C 15/06
[58] Field of Search ............................ 340/183, 206

[56] References Cited
UNITED STATES PATENTS

| | | | |
|---|---|---|---|
| 3,132,329 | 5/1964 | Penter | 340/183 |
| 3,249,883 | 5/1966 | Bernecke | 340/183 |
| 3,626,398 | 12/1971 | Owens | 340/183 |
| 3,665,399 | 5/1972 | Zehr | 340/183 |

Primary Examiner—Thomas B. Habecker
Attorney, Agent, or Firm—Richard S. Sciascia; Paul N. Critchlow

[57] ABSTRACT

A low-power, transient-free, multi-channelled bio-telemetry system utilizes a series of C/MOS switches coupled to the data sampling electrodes. Shift register pulses selectively enable the switches to sequentially shift the data sample inputs through nine, switch-controlled channels. The switches have little battery drain and, due to their N and P complimentary arrangement, their gating pulses are effectively cancelled and removed from the system channels. Multiplexing precedes amplification by applying switch outputs to a single, low-power amplifier. A special pulse position modulator employing a ramp generator circuit provides the pulse trains to a keyed transmitter. Other significant improvements including a unique shift register arrangement with a synchronizing interval permit long periods of continuous operation undisturbed by the need for battery changes. The transmitted data is received by a suitable demodulating receiver to produce a recordable output for evaluation and computer analysis.

11 Claims, 4 Drawing Figures

LOW LEVEL BIO-TELEMETRY SYSTEM USING C/MOS MULTIPLEXING

BACKGROUND OF THE INVENTION

The present invention relates to multiplexed telemetering systems and, in particular, to low-power bio-telemetry systems for obtaining EEG and other physiological data.

In recent years, a number of telemetry systems have been developed for obtaining physiological data from conscious, unrestrained individuals or animals. For the most part, the development effort has been directed toward the problem of providing compact, lightweight and low-power equipment which can be mounted, for example, on the individual's head with the individual free to move about unencumbered by trailing wires and other disturbing influences. Examples of such prior systems are described in the following publications: "A Four Channel Integrated Circuit Telemeter for Seizure Monitoring", R. W. Vreeland and C. L. Yeager, Digest of 7th International Conference on Medical and Biological Engineering, 1967, Stockholm, Sweden; "A Compact Six-Channel Integrated Circuit EEG Telemeter", Vreeland, Yeager and Henderson, Jr., Electroencephalography and Clinical Neurophysiology, Elsevier Publishing Company, Amsterdam, 1971, 30:240–245; and "A Multichannel Implantable Telemetry System", Medical Research Engineering, March-April, 1969 by Fryer, Sander and Datnow.

Although these prior systems have been most helpful, there is a continuing need for improvement. In particular, it is highly desirable to provide bio-telemetric systems which can be physically mounted on the subject to be studied and which then are capable of continuously operating for unusually long periods of time without any need for battery changes or other similar maintenance. As will be appreciated, the desire for a lengthy period of undisturbed operation is based upon the benefits which result when the subject of the study is permitted to function throughout the entire period in an undisturbed and unrestrained manner. Obviously, the long periods require the development of systems having unusually low-power consumption. In particular, the power consumption should be such that the need for battery changes can be avoided at least for overnight periods and, preferably, for periods extending for several or more days. Aside from the need for the longer operating periods, other recognized needs include the provision of more available channels for the studies as well as a reduction in the size of the instrumentation and the simplicity of its circuitry. In conventional multi-channel systems one of the factors contributing to power consumption is a separate amplifier for each of the channels with the multiplexing being performed subsequent to the amplification. Such arrangements apparently have been considered necessary to obtain a suitable signal level for the multiplexing. As will be described, a feature of the present system is the use of a single amplifier for all channels. In other words, the present system permits multiplexing at the amplifier input. However, this type of multiplexing imposes another problem in that the gating pulses needed to establish the channels then may be coupled into the channels. This undesired coupling will be recognized as unacceptable when it is considered that, for example, the gating pulses may be in the order of 6 volts while the data sample signals which are to be measured and analyzed by the system may be about $100\mu v$. Such a signal to noise ratio effectively denies the production of any worthwhile data.

The present invention resolves this transient coupling problem by employing special complimentary, metal oxide semiconductor (C/MOS) switches to perform the multiplexing prior to amplification by a single amplifier. As is known, the C/MOS switches utilize and "N" channel FET in parallel with a "P" channel FET and the enabling or gating of these C/MOS switches requires pulses of opposite polarity. Because of the opposite polarity, the portions of the gating pulses that otherwise would be coupled into the channel are effectively cancelled. The invention further employs a particular pulse position modulation for the amplified output as well as other particular features which significantly reduce the power requirements. For example, the system employs a clock-controlled shift register to provide a synchronizing interval or spacing as contrasted with the need for a separate synchronizing pulse.

DETAILED DESCRIPTION OF THE DRAWINGS

The invention is illustrated in the accompanying drawings of which:

DETAILED DESCRIPTION OF THE INVENTION

The present system is particularly adapted for use in depth electrode studies of epileptics. However, because DC amplification is employed, it can be used to telemeter such data as temperature, respiration, blood flow, blood pressure, the electrocardiogram and galvanic skin resistance, as well as the electroencephalogram. Appropriate imput transducers, of course, must be used. Also, in scalp electrode recording, as contrasted with depth electrodes, low level pre-amplifiers should be used and these amplifiers may be of the type shown and described in the Vreeland et al publication entitled "A Compact Six-Channel Integrated Circuit EEG Telemeter".

Physically considered, the system is capable of being packaged in a relatively small, compact arrangement which, for example, may be in the form of two plastic boxes glued together in an open book configuration. Each of the packages, for example, may be about 1.2 cm × 3.5 × 4.5 cm boxes. Such a configuration is designed to fit under the outer head bandages of an epileptic with implanted depth electrodes.

Figure 2:
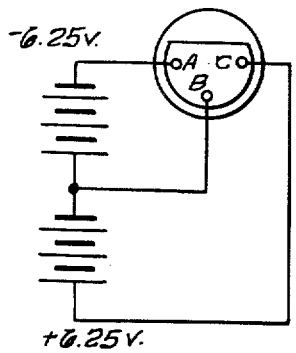
FIGS. 2 and 3 are circuit diagrams of the battery connector arrangement of the system.
Figure 3:
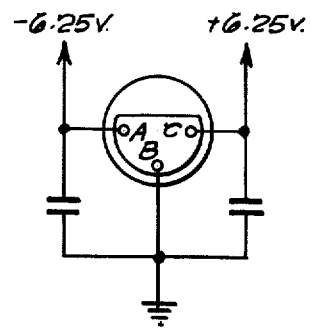

The system is battery powered preferably by a plug-in battery pack which may consist of 10 Burgess CD2 cells potted in epoxy in a 1.7 cm × 3.2 cm × 3.8 cm box. Longer battery life can be achieved by using disposable mercury batteries, such as two Burgess H146X batteries. Such disposable mercury batteries, for example, have been operated continuously for a period of about 13 days and nights. However, a battery pack using the rechargable cells will provide up to 18 hours of continuous operation. To couple the battery power, ten SM3S Winchester connectors (FIG. 2) can be used along with mating SM3P Winchester plugs (FIG. 3). Preferably other connectors are used for the electrodes which may be either needle or disc.

Figure 1:
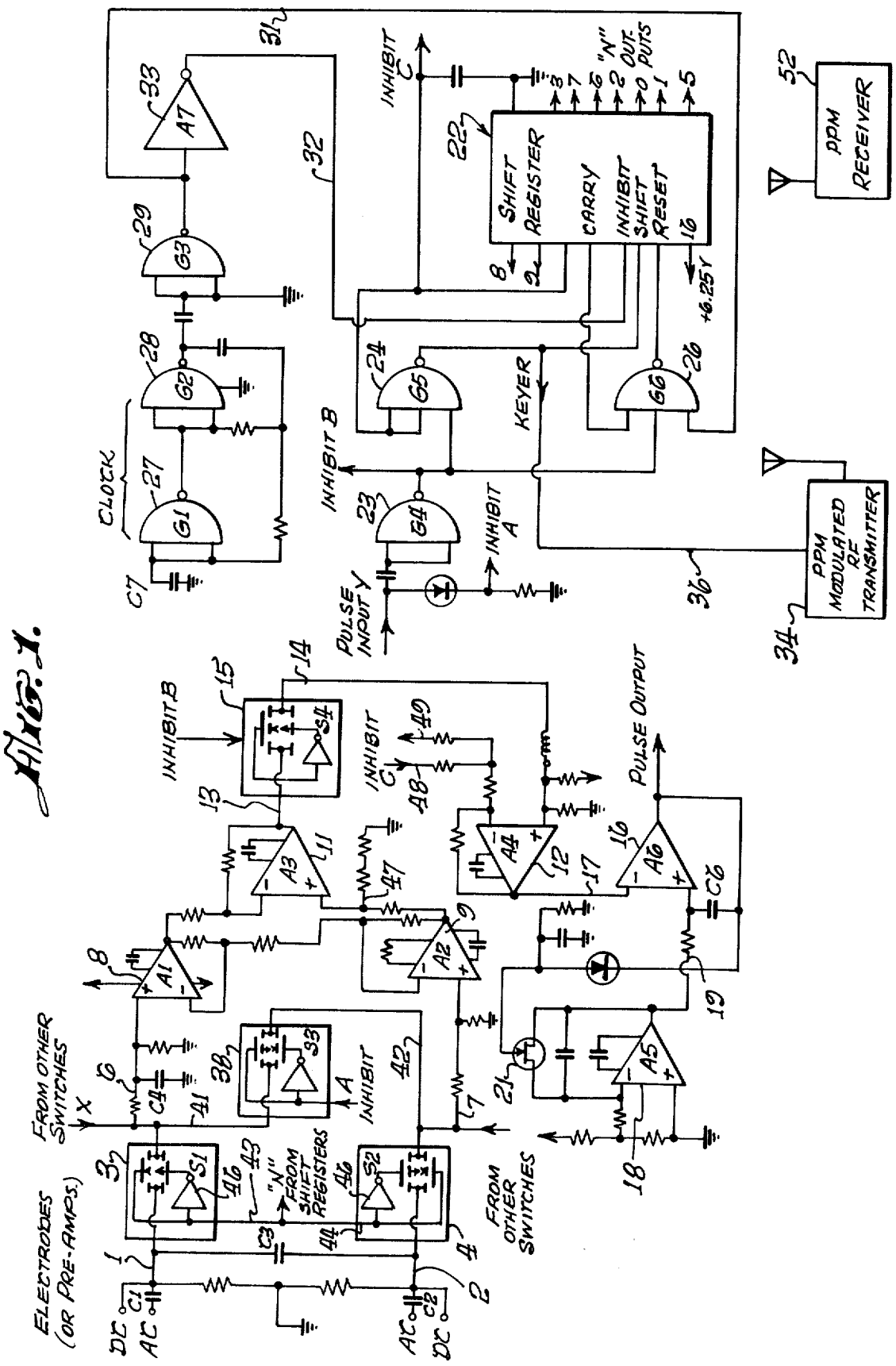
FIG. 1 is a schematic block diagram of the present system.

The system is, as already stated, a multi-channel system deriving its input from a number of selectively located electrodes. Each pair of electrode, of course, represents a separate channel having input conductors 1 and 2 as shown in FIG. 1. The illustrated implementation is for a nine channel system, although the number of channels can be increased or decreased as desired. Further, the system is designed for bipolar as well as monopolar recording from all nine channels and, for this reason, differential inputs are provided for each channel. FIG. 1 illustrates only one channel since the remaining eight channels essentially are duplicates. Further, each channel can be coupled to AC or DC. However, when the system is to be used for monitoring low frequency phenomena non-polar input blocking capacitors such as capacitors $C_1$ and $C_2$ can be used. Before considering the circuit details it may be helpful to generally review and identify the major components of the system. Accordingly, as shown, differential electrode inputs are applied through conductors 1 and 2 to a pair of switches 3 and 4 which are of the C/MOS type having the N and P characteristics already briefly considered. The arrangement utilizes nine pair of switches 3 and 4 to gate electrode data samples through conductors 6 and 7 to a single broadband amplifier arrangement which includes amplifiers 8 and 9, and a differential amplifier 11. As will be noted in FIG. 1, conductors 6 and 7 are coupled to all of the other switches through conductors x and z. Thus, multiplexing is achieved at the input of the broadband amplifier or, in other words, only one broadband amplifying means is required for this system. The output of differential amplifier 11 is applied through conductor 13 to another C/MOS switch 15 that gates the amplified pulse train derived from the differential amplifier to a driver amplifier 12 by way of conductor 14.

Driver amplifier 12 applies its output through conductor 17 to a comparator 16 which is provided with the customary pair of inputs one of which is the inverting input derived from driver amplifier 12. This input sets a reference level for the comparator. The function of the comparator is to compare the reference level with an input derived from a ramp generator 18 through input conductor 19. When the ramp applied to the comparator through conductor 19 runs up to the level of the reference established by the driver amplifier, the comparator flips to a positive output which removes a holdoff bias applied to ramp generator 18 by an N-channel Motorola NMT 3823 field effect transistor 21 which resets the ramp generator. A capacitor C6 determines the positive output pulse duration of the voltage comparator. This arrangement of the driver amplifier, the comparator and the ramp generator constitutes pulse position modulation of the sequential pulse train derived from the pulse samples. Operationally considered, the reference level of the comparator is set by the instantaneous amplitude of the data being sampled so that variations in the time required for ramp to run up to the fixed reference level will vary only in accordance with the amplitude of the data sample or, more specifically, with the amplitude of each pulse in the data sample pulse train. Consequently, the positive short pulse outputs of the comparator are variably positioned in time in a manner that is directly proportional to the amplitude of the data sample. Thus, if the system is employing a sampling rate of 312 pulse trains per second which, as will be explained, is the intended sampling rate of the system, output pulses of the comparator can be quite short. A particular advantage of this ramp-generated pulse modulation technique is its low duty cycle which materially reduces power consumption.

The pulse train output of comparator 16 is identified in the drawing as pulse input Y coupled to a shift register 22 through a gating arrangement including gates 23, 24 and 26. Gate 24, as shown, is coupled directly to a so-called register 'shift' input while gate 26 provides an input for a so-called 'reset' register position. A clock arrangement including gates 27 and 28 is operated as a free-running or astable multivibrator to control the sampling rate of the system which, as has been stated, may be in the order of 312 pulse trains per second.

It will be noted that register 22 provides ten output positions numbered 0–9 which also are identified as 'N' outputs. These 'N' outputs each are coupled to the pairs of switches represented in FIG. 1 by switches 3 and 4 and their function is to trigger the switches by providing switch-enabling pulses. If for example, it is considered that the pair of switches 3 and 4 represents channel 1 of the system, the arrangement may be one in which the 'O' on the shift register turns on channel 1, while the '1' of the register turns on channel 2, etc. As will be explained, '9' on the register inhibits gate 24 so that no more pulses are transmitted until the shift register is reset.

Considering the shift register circuitry in greater detail, pulse input Y, prior to being applied to the register 'shift' position is differentiated and inverted twice in gates 23 and 24 which, respectively, may be CD4001 and CD4000 components. Each pulse in pulse input Y triggers the shift register to shift it one step thereby enabling, as already stated, a different pair of amplifier input switches. The inverted output of gate 23 is applied as an input to gate 26, which also may be a CD4000 three input NAND gate, used to generate the reset pulse. NAND gate 26 generates the reset pulse only if all three of its inputs are "low", this requirement preventing premature resetting of the shift register. The inputs of gate 26 are, as stated, the inverted input from gate 23 as well as a clock input which has been differentiated and inverted in a gate 29. As shown, the output of gate 29 is applied through conductor 31 to gate 26. The third input for NAND gate 26 is a 'carry' pulse which, in the present implementation is used to keep its input to gate 26 'high' during the first few shifts of the shift register. At a particular shift, such as the fifth shift the 'carry' goes 'low'. When the register shifts to position 9, pulse input Y as well as the 'carry' input are 'low'. Consequently, when the inverted clock pulse derived from gate 29 is applied to the NAND gate, the register resets to 0 to initiate a new train of pulses. This arrangement is advantageous particularly since it permits the use of a synchronizing space or time interval in contrast to a specially generated synchronizing pulse which normally is used but which serves only to further complicate the circuitry and add to the power requirements. The clock, of course, controls the synchronizing space interval and, in doing so, maintains the desired 312 pulse trains per second sampling rate. It also will be noted that register 22 has an 'inhibit'position coupled by conductor 32 to an inverter 33 which re-inverts the output of gate 29 of the clock arrangement. This 'inhibit' pulse is used as an inhibit toggle after reset.

Figure 4:
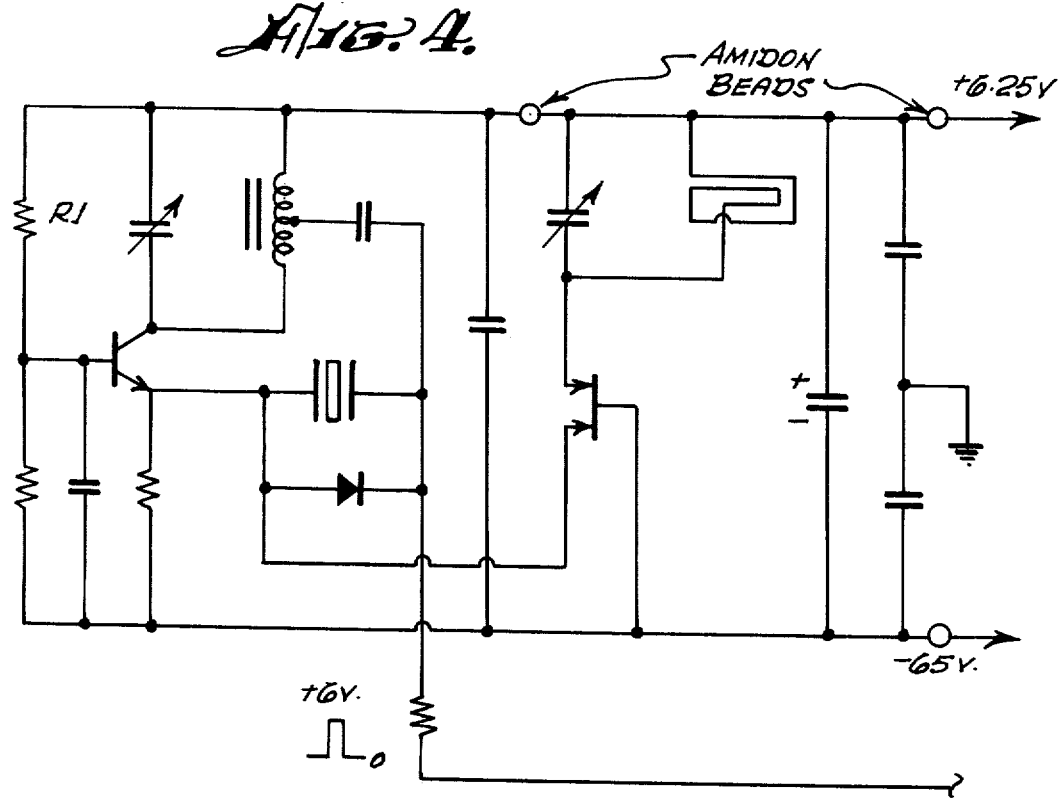
FIG. 4 is a circuit diagram of a suitable transmitter.

The modulated pulse train output from gate 24 is used to key a transmitter 34 shown in block form in FIG. 1, this output being applied to the transmitter by a conductor 36. A suitable transmitter circuit is shown in FIG. 4 and subsequently will be considered in some detail. As also will be noted, gate 24, in addition to re-inverting the output of gate 23, is a 3-input NAND gating component having inputs from gate 23 and from the '9' signal from the shift register. Thus, this gate is inhibited during the synchronizing interval of the register by the '9'signal from the register. It should be noted that an inhibit signal 'C' simultaneously is derived from the register and that this inhibit 'C' is applied to driver amplifier 12 to inhibit this amplifier during the syhchronizing interval.

Other inhibit signals identified in FIG. 1 as inhibit 'A' and inhibit 'B' are derived, respectively, from the pulse train arriving at gate 23 and from the inverted output of gate 23. In a manner that will be described, inhibits 'A' and 'B' are used to short circuit the input to broadband amplifier 8, 9 and 11 during the switching intervals and also during the switching intervals to remove switching transients from the output of the broad band amplifier. Inhibit A is applied to a switch 38 coupled between each pair of the input channel switches represented by switches 3 and 4. Inhibit 'B' is a negative-going pulse applied to previously-identified switch 15 coupled between the broadband amplifier and driver amplifier 12.

Considered in greater detail, switch 38, which preferably is a C/MOS type of complimentary FET switching arrangement, is coupled between output conductors 41 and 42 of switches 3 and 4 respectively. Switch 15, in turn, is used to couple conductor 13 to driver amplifier 12. The need for switches and 15 and 38 becomes more apparent when it is recognized that the data sample signals which the system is attempting to detect and measure are at a level of about 10 $\mu v$ while the gating pulse signals used to gate switches 3 and 4 are about 6 volts. Obviously, if any significant portion of the gating pulse is coupled into the channel it would create an impossible detection situation. In this regard, it should be kept in mind that the present system basically employs low level input switching and multiplexing at the amplifier input to achieve the low level switching, it is essential that the gating pulses effectively be removed rather than amplified. Gate 15 removes the remaining transients which, although quite small, nevertheless may be about 50 millivolts or about 500 times the data sample level being measured.

The ability to effectively remove the gating pulses and their transients from the channels is one of the features of the present invention and for the most part, the removal is achieved by the use of the complimentary, MOS/FET switches.

As is known, a complimentary MOS switch is a commercially-available component such as the R.C.A. CD 4016 switch. These switches are available as CD 4016 flat packs and, since each pack contains four switches, only five of the packs are required. The R.C.A. switches are known in the trade as "COS/MOS" switches. A more general designation is C/MOS. Each of the switches in the flat pack has an "N" channel FET in parallel with a "P" channel FET and the required gating pulses are of opposite polarity. Consequently, the portions of the gating pulses that are coupled into the channel effectively cancel. This effective cancellation apparently is not generally recognized but it has been found to be effective for use in circuitry such as that used in the present system. In particular, it should be noted that FET switches have been tried and found to be unsatisfactory. Apparently they permit the gating pulse to be coupled into the channel via the gate-channel capacitance. Thus, the capacity of the present system to remove the gating pulses from the channels is achieved primarily by the cancellation feature of the COS/MOS switches.

A further feature is that the switches are short circuited during switching intervals. As noted, the timing is achieved by the use of inhibit signal 'A'. Also, the transient removal achieved by switch 15 is controlled by a negative-going pulse during the switching intervals. This combination of input short circuiting and output gating effectively removes all switching transients. The circuit arrangement for the C/MOS switches is generally illustrated in the drawing. As will be noted, the "N" pulses received as outputs from shift register 22 are applied to the "N" and "P" channels of each switch by conductors 43 and 44. The positive 'N' input has its polarity reversed by an inverter 46 before being applied to the 'P' channel of the switch.

Briefly summarizing, the present system combines a number of related features in such a manner that the power consumption can be unusually low so as to permit long, unattended periods of operation. The C/MOS switches permit low level switching prior to amplification by effectively cancelling the gating pulses. The single amplifier is a significant power conservation feature as is the modulation technique, the use of the register's synchronizing interval and the use of the clock-controlled register itself. Even so, it will be obvious that the obtaining of the maximum advantages also depends upon the selection of components. Some attention therefore should be directed toward the particular components.

As to the single broadband amplifier, the component used in the illustrated system is one having a frequency response from DC to better than 100 KHZ which is needed because multiplexing is done by switching the amplifier input. National Semiconductor NH0001ACF operational amplifiers may be used in a manner that, for example, provides a gain of about 120 with an input resistance of approximately 200 k ohms and a common mode rejection ratio of at least 60 dB. The common mode rejection is adjusted by selecting resistor 47 identified in FIG. 1. The use of a differential amplifier with good common mode rejection permits bipolar as well as monopolar recording from all nine channels.

As has been noted, the main amplifier consists of two operational amplifiers previously identified as amplifier 8 and 9 operating as followers with gain followed by a differential amplifier 11. Obviously, it is desirable to achieve the amplification with a minimum of power requirements and the components which have been described satisfy this purpose. A National Semiconductor LI 44 also can be used to advantage. Driver amplifier 12 is a non-inverting monopolar amplifier with selectable gain. The gain and DC bias are determined by resistors 48 and 49 which may be mounted on the SM3P Winchester plug shown in FIG. 3. This arrangement permits the system gain to be easily changed to accommodate different types of inputs signals.

The pulse position modulation achieved by comparator 16 and ramp generator 18 has been described in some detail and generally may be provided by conventional components. As has been indicated, its operation is one in which the comparator is saturated with a negative output until flipped to a positive output by the ramp following which positive feedback capacitor 51 holds the comparator for about 17 $\mu s$. This 17 microsecond pulse then passes through gates 23 and 24, already identified as NAND gates, to shift the register and key the transmitter. Resetting of the register to maintain the desired sampling rate is achieved by the clock provided by gates 27 and 28 and, as stated, the clock circuitry is in effect in astable multivibrator such as is described by J. A. Dean in RCA Application Note ICAN-12-67. As further shown in FIG. 1, the keyed transmission of the data sample pulse train in its modulated form is transmitted to an PPM receiver 52 which converts the pulse position modulation to pulse width modulation. A suitable receiver is an Astrocommunications Laboratory SR-209 with a 300 KHz bandpass. This receiver utilizes a shift register demodulator to convert the modulation to pulsewidth modulation and its arrangement is described in some detail in the previously referenced publication "A Compact Six-Channel Integrated Circuit EEG Telemeter". The output of the demodulator receiver is recorded and evaluated in any desired manner.

A suitable transmitter for use with the present system is shown in FIG. 4. Transmission is the major power consumer in the system and its power requirements should be minimized by arrangements employing, for example, a series switch to remove all power between pulses. Power is 'on' for only very short pulses. Suitable transmitters are commercially available and one such transmitter is a Motorola MM4018 transistor operating as a power oscillator in the 88 MHz to 108 MHz FM broadcast band. The resulting low duty cycle pulse modulation greatly reduces the power consumption. As will be noted, all of the C/MOS circuits are powered by a positive 6.25 volt supply. The power sources may be connected in series to provide 12.5 volts for the transmitter. The same sources provide +6.25 volts and −6.25 volts for the operational amplifiers and, if used, for the scalp electrode preamplifiers.

The system performance for depth electrode recording when tested with a 10 k ohm source is: Crosstalk 30dB down, noise level 5 to 13 microvolts RMS (determined by noise level in the receiving amplifier), maximum input ±1 millivolt, frequency response 0.2HZ to 150HZ, input impedance 200K ohms, common mode rejection 60dB. With scalp electrode pre-amplifiers, the performance is: noise level one microvolt RMS, input impedance one megohm, and common mode rejection 70dB.

In actual operation, the described system powered by throwaway mercury batteries has permitted continuous use for a period of 13 days. Rechargeable batteries easily achieve unattended overnight operation and, of course, this period of continuous operation is dependant upon the type of battery used. Broadly considered, the improved operation achieved by the system is premised upon the low level switching which, in turn, is permitted by the use of the C/MOS switch arrangement. Nevertheless, the other components and their arrangements, such as the gating pulse and transient removal techniques, are important factors which contribute significantly to the ability of the system to detect the low level signals as well as its low power consumption capability.

Obviously many modifications and variations of the present invention are possible in the light of the above teachings. It is therefore to be understood that within the scope of the appended claims the invention may be practiced otherwise than as specifically described.

I claim:

1. A multi-channel biotelemetry system for multiplexing and transmitting individual data samples derived as signal inputs from a plurality of electrode sources, comprising:
   a plurality of complimentary-type MOS switching mechanisms receivably-coupled one to each said data samples, said mechanisms being sequentially operated for cumulatively providing an output pulse train formed of said electrode source samples
   broadband main amplifying means receivably coupled to said output pulse train,
   pulse-position modulating means receivably-coupled to said amplified train for producing a sequence of output pulses spaced one from another a distance directly proportional to the amplitude of each pulse of said train,
   transmitter means coupled to said modulated output,
   resetable pulse-generating means for sequentially operating said plurality of switching mechanisms, said means being responsively coupled to said modulated pulse train for generating a separate switch-enabling pulse for each successively-received pulse, and
   means for synchronizing the resetting of said pulse-generating means after said switching mechanisms have been sequentially enabled.

2. The system of claim 1 wherein each of said complimentary MOS switching mechanisms includes:
   an N-channel switch,
   a P-channel switch, and
   a circuit coupling said switch-enabling pulses in parallel to said N and P channel switches,
   said parallel connections of one of said switches including an inverting means whereby a pulse of one polarity enables one of said switches and an opposite polarity pulse enables the other switch whereby the enabling pulse effectively cancels.

3. The system of claim 1 wherein said pulse position modulating means includes:
   a comparator means having a pair of inputs and an output,
   a driver amplifier for setting a reference voltage level for the comparator,
   said driver amplifier having an input receivably coupled to said amplifying means and an output coupled to one of said comparator inputs so that said reference level of the comparator varies directly with the amplitude of each pulse of said pulse train,
   a ramp generator coupled to the other input of said comparator whereby the time required for said generated ramp to reach said comparator level is directly proportional to the amplitude of each pulse of said train,
   said comparator producing said pulse position modulated pulses at said reference level,
   means for setting the time duration of said comparator output pulse, and
   hold-off biasing means for said ramp generator, said comparator output resetting said ramp generator by removing said bias.

4. The system of claim 1 wherein said resettable pulse generating means includes:
   a pulse-generating shift register means having a plurality of pulse outputs each coupled to a separate one of said switching mechanisms and a 'shift' input responsively coupled to said data sample pulse train, said register shiftably applying a switch-enabling pulse responsively with the receipt of each successive pulse of said train to a successive one of said register outputs, whereby said switching mechanisms are sequentially enabled to produce said data sample pulse train.

5. The system of claim 4 wherein said shift register further includes:

clock-controlled means for resetting said register after said switching mechanisms have been enabled;

said means being responsive to the coincidence of a final pulse of said pulse train and a clock pulse;

said resetting again applying a switch-enabling pulse to the first of said sequentially-enabled switching mechanisms for initiating a second data sample train, and said coincidence being timed to provide a synchronizing time interval space between successive pulse trains.

6. The system of claim 4 further including:

pulse generating means associated with said shift register means for generating 'inhibit' pulse upon the receipt by said register means of said final pulse, said 'inhibit' pulse inhibiting transmission of signals to said "shift" input during said synchronizing interval.

7. The system of claim 4 further including:

a pulse-enabled switch means coupled into said system between each of said complimentary MOS switching mechanisms and said main analyzing means for shorting each of said main amplifier during the shifting of said shift register.

8. The system of claim 7 further including:

a second pulse-enabled switch means coupled as a data sample transmission gate into said system between said main amplifying means and said modulating means, said switch means being opened during the shifting of said register means for removing switching transients from said modulation.

9. The system of claim 8 wherein said first and second switch means are complimentary MOS mechanisms including a pair of N and P channel switch members coupled in parallel with each member being activated by a pulse of opposite polarity, said activating pulses being derived from said pulse train.

10. The system of claim 7 wherein each of said data sample inputs is bipolar and a pair of said sequentially-operated switching mechanisms are provided for each data sample, said second pulse-enabled switch means being coupled between the outputs of said pair for shorting said pair during said shifting of said register means.

11. The system of claim 10 wherein the second switch means is a complimentary MOS mechanism.

* * * * *